United States Patent [19]

Abenaim

[11] Patent Number: 5,235,964
[45] Date of Patent: Aug. 17, 1993

[54] FLEXIBLE PROBE APPARATUS

[75] Inventor: Daniel Abenaim, Lynnfield, Mass.

[73] Assignee: Analogic Corporation, Mass.

[21] Appl. No.: 803,158

[22] Filed: Dec. 5, 1991

[51] Int. Cl.⁵ .......................... A61B 1/06; A61B 8/12
[52] U.S. Cl. ..................................... 128/4; 128/662.06
[58] Field of Search ...................... 128/660.03, 662.06, 128/4–9; 73/623

[56] References Cited

U.S. PATENT DOCUMENTS

| | | | |
|---|---|---|---|
| 4,580,551 | 4/1986 | Siegmund et al. | 128/4 |
| 4,773,395 | 9/1988 | Suzuki et al. | 128/4 |
| 4,906,230 | 3/1990 | Maloney et al. | 128/4 X |
| 4,911,148 | 3/1990 | Sosnowski et al. | 128/4 X |

Primary Examiner—Francis Jaworski
Attorney, Agent, or Firm—Schiller & Kusmer

[57] ABSTRACT

A flexible, manipulatable, an reuseable probe apparatus is disclosed wherein a double sleeve probe housing comprises a relatively thin, slippery outer sleeve and a thicker, more resilient inner sleeve having a plurality of apertures in at least a portion of its side wall. By reducing the stress and strain on the wire control system used to manipulate the probe, the probe apparatus of this invention has a substantially extended useful life.

25 Claims, 2 Drawing Sheets

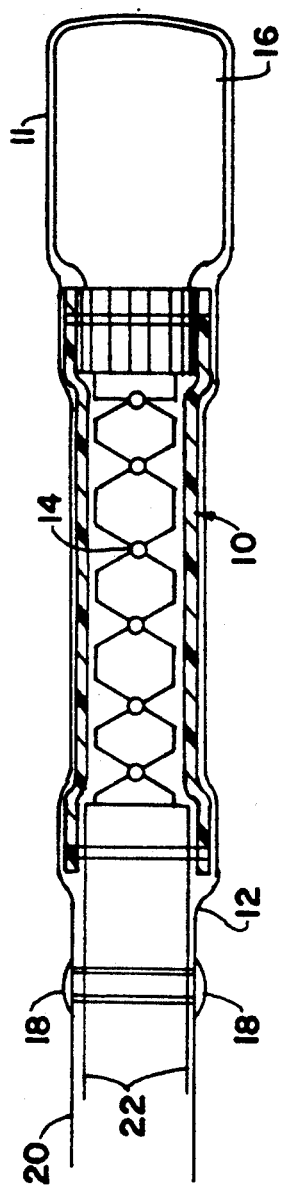
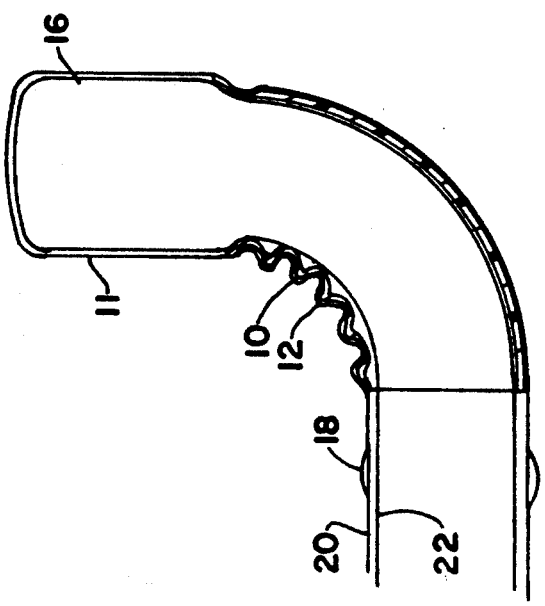
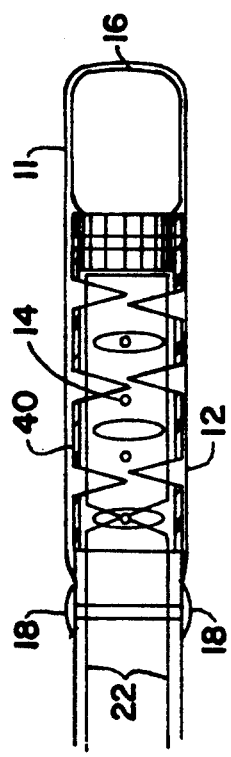

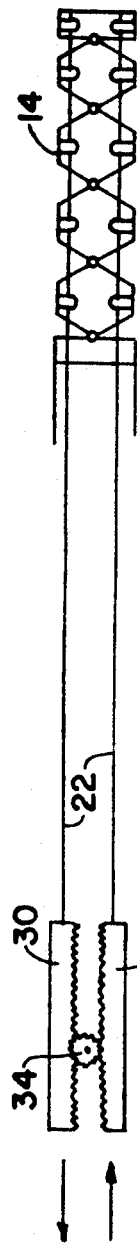
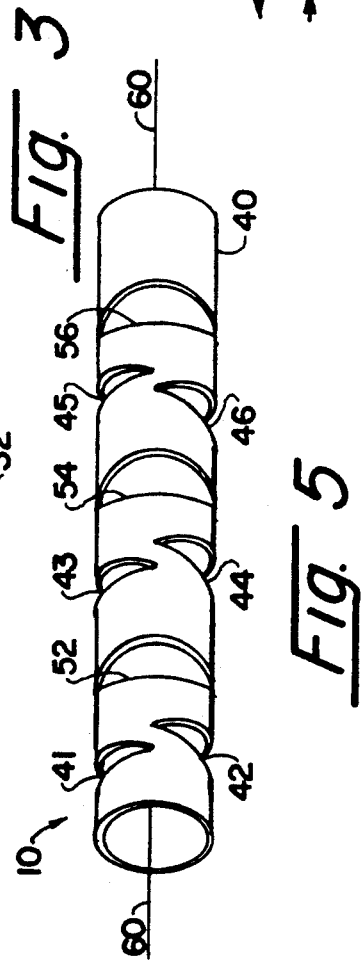
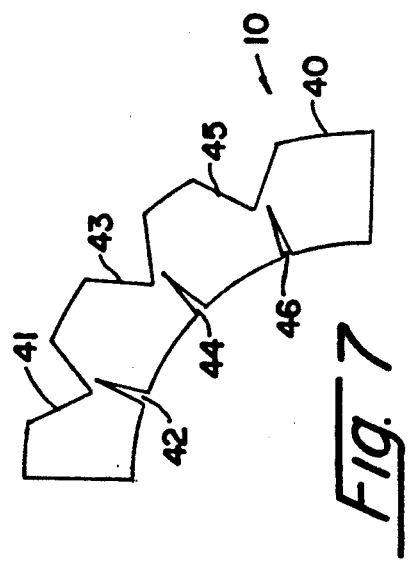
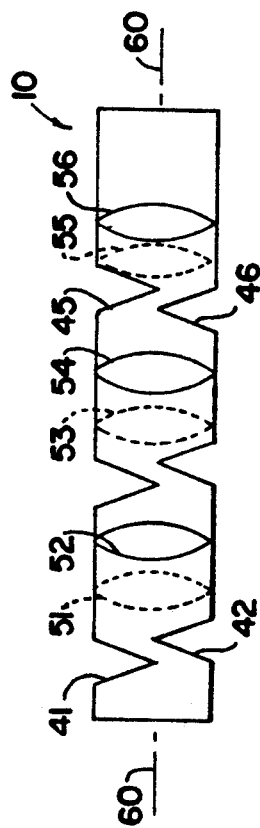

FLEXIBLE PROBE APPARATUS

BACKGROUND OF THE INVENTION

This invention relates generally to a probe apparatus, such as an ultrasound transesophageal probe for insertion to the stomach via the mouth and throat for subsequent manipulation, by means of a wire system, for imaging the heart and other internal bodily organs. Such apparatus is well-known in the art. A key requirement for such a probe is that the wire control system must enable movement of the head of the probe over a wide range of positions with as small a radius of curvature as possible.

The internal probe mechanism, including the external electrical leads and control wires of such a system, must be completely insulated from bodily contact by a surrounding jacket or boot. However, the completed probe apparatus, typically comprising an articulate mechanism, 124 coaxial cables connected to two transducers, and the aforementioned jacket or boot, is a relatively rigid system that puts enormous strain on the wire control system commonly leading to excessive fatigue and premature failure. Such probe apparatuses, which may cost up to $30,000–40,000, often experience premature failure after just a few thousand activations due to control wire fatigue. For economy and efficiency, it is desirable to increase the useful life of these probes by tenfold or more.

In general, it is well-known in the art to use sleeves, boots or jackets of various types in connection with a wide range of medical instruments that are intended to be utilized inside the body. Such sleeves, boots or jackets may be variously employed to facilitate insertion of the instrument into the body, to shield the body from the instrument and vice versa, to supply fluid to an internal site, and many other such applications. In some of these applications, the prior art teaches the use of a catheter wherein at least some portion of the catheter includes a plurality of apertures in the side wall of the catheter. In these devices, however, the apertures serve no function other than to permit drainage of fluid from the body through the catheter or, alternatively, for supplying fluid through the catheter to some internal body site.

Representative of this type of prior art are U.S. Pat. Nos. 1,786,373 (Walker—note FIG. 1, apertures 20); 3,595,241 (Sheridan—note FIG. 1, apertures 12); 3,905,361 (Hewson et al.—note FIG. 1, apertures 3); 4,748,984 (Patel—note FIGS. 1 and 2, apertures 29); 4,781,678 (de Couet et al.—note FIGS. 1, 2 and 3, apertures 4); 4,804,358 (Karcher et al.—FIG. 1, apertures 18); 4,813,929 (Semrad—FIG. 6, apertures in chest tube 20; FIG. 7, apertures 38); 4,955,384 (Taylor et al.); 4,990,133 (Solazzo—FIG. 1, drainage orifices 16; FIG. 2, irrigation ports 25). It should be noted that there is no suggestion in these patents of a need for greater flexibility in the catheter systems, nor is there any teaching of employing the inner catheter of a double-catheter system in order to increase flexibility.

U.S. Pat. No. 4,291,694 (Chai) is directed to another type of catheter apparatus used in connection with thoracic surgery. Pneumotube 10 (FIG. 1) includes a proximal portion 11 having a plurality of rows of small apertures 14. According to Chai, the size and arrangement of apertures 14 should be selected such that this portion of the pneumotube "will have sufficient rigidity . . . but also have sufficient flexibility to conform to the chest wall as the patient's lung expands, "(col. 3, lines 54–61).

U.S. Pat. No. 4,661,094 (Simpson) is directed to a perfusion catheter for positioning in a partially occluded blood vessel. Tubular member 16 (FIGS. 2 and 3) is provided with a plurality of holes 24 that "are spaced apart longitudinally . . . and are also spaced circumferentially . . . " (col. 2, lines 15–17). More particularly, "each successive hole is offset by 90 degrees with respect to the preceding hole," (col. 2, lines 26–27). The purpose of the 90 degree offset configuration in Simpson is clearly to facilitate drainage. There is no suggestion in Simpson that this aperture configuration has any beneficial effects with respect to flexibility. There is also no teaching in Simpson of a double catheter system.

U.S. Pat. No. 4,576,772 (Carpenter) is directed to a multi-lumen catheter having filled "notches" (FIG. 1, notches 17; FIG. 2, filled notches 19) to add greater flexibility to the catheter. Specifically, the notches in the Carpenter catheter are filled "with a vulcanizable polymer material having a hardness when cured less than the hardness of said plastic tube whereby the resistance to bending of said tube is reduced" (col. 1, lines 55–58). Carpenter requires that the notches be filled in order to maintain a fluid-tight catheter (col. 1, lines 47–48 and 65–66). Carpenter uses the multiple lumens of his catheter as ducts or feeding tubes to provide the polymeric filler to the notches (col. 2, lines 42–47). According to Carpenter "[t]he resultant assembly . . . provides an articulatable catheter section or length that flexes readily with less stress and strain on the control wires as they are operated to deflect the distal end of the scope with which the catheter is used," (col. 2, lines 63–68). But, the Carpenter catheter is a relatively inexpensive and disposable system that is neither designed for nor capable of accommodating an articulate mechanism and 124 coaxial instrumentation cables as required for an ultrasonic probe apparatus. Thus, nothing in the Carpenter patent suggests how to overcome the rigidity problem associated with ultrasonic probes or teaches how to increase the useful life of these extremely expensive devices by minimizing premature fatigue of the control system.

Some of the more common approaches to the general problem of increasing flexibility in a tubular system have proven completely inapplicable to the specific case of a transesophageal probe. For example, flexibility of the probe system could be increased by using larger, looser-fitting sleeves or a bellows-style sleeve construction to contain the articulate mechanism, control wires, and 124 coaxial cables. The trade-off, however, is that the resultant system would be larger in diameter and, therefore, more difficult to insert through the esophagus. Similarly, a tight, slippery outer surface makes it easier to insert the probe, whereas a loose or bellows-style surface would impede insertion. Sleeves comprising concentric or articulated ring structures could also be used to increase flexibility, but again only at the cost of unacceptably increasing the size of the device and decreasing the ease with which the device can be inserted.

These and other problems with and limitations of the prior art transesophageal probes are overcome with the flexible probe system of this invention.

OBJECTS OF THE INVENTION

Accordingly, it is a principal object of this invention to provide a flexible probe apparatus having increased longevity.

It is also an object of this invention to provide a protective sleeve system with improved flexibility for housing a transesophageal probe or comparable medical instrumentation.

A further object of this invention is to provide a double sleeve system for housing a medical instrument wherein at least one end of the inner sleeve comprises a series of apertures designed to increase the flexibility of the system.

Still another object of this invention is to provide a transesophageal probe apparatus wherein the inner sleeve of a double sleeve housing comprises apertures of particular size, shape and spacing in order to minimize the resistance to bending.

These and other objects and advantages of this invention will be better understood from the following description, which is to be read together with the accompanying drawings.

SUMMARY OF THE INVENTION

The probe apparatus of this invention comprises a double sleeve housing including a relatively thin and slippery outer sleeve or boot and a thicker, more resilient inner sleeve having a plurality of apertures in at least a portion of its side wall. As a result of this invention, less stress and strain is put on the wire control system used to internally manipulate the head of the probe thereby substantially prolonging the useful life of the probe by as much as ten times as compared with conventional transesophageal probes.

BRIEF DESCRIPTION OF THE DRAWINGS

FIG. 1 is a schematic cross-sectional view, partially cut away, of a transesophageal probe in the straight (unbent) position without apertures in the inner sleeve.

FIG. 2 is a schematic view, partially cut away, of a transesophageal probe, as in FIG. 1, wherein the held of the probe has been bent at about a 90 degree angle with respect to the axis of the probe.

FIG. 3 is a schematic view of a conventional rack and pinion system used to control a transesophageal probe.

FIG. 4 is a schematic view, partially cut away, illustrating how the rack and pinion system of FIG. 3 can be used in combination with an articulate mechanism to bend the head of the probe as shown in FIG. 2.

FIG. 5 is a schematic isometric view of a portion of the apertured inner sleeve of the probe apparatus of this invention.

FIG. 6 is a side elevational view of a portion of the apertured inner sleeve of the probe apparatus of this invention.

FIG. 7 is a side elevational view of a portion of the apertured inner sleeve as in FIG. 6 but showing the sleeve bent at about a 90 degree angle with respect to the axis of the probe.

FIG. 8 is a schematic partial cross-sectional view showing a portion of the apertured inner sleeve in combination with the rest of the probe apparatus of this invention.

DETAILED DESCRIPTION OF THE DRAWINGS

FIG. 1 is a schematic, cross-sectional view showing a transesophageal probe unit in an unflexed position without apertures in the inner sleeve. A relatively thin and slippery outer sleeve 12 and a thicker, softer, and more resilient inner sleeve or boot 10 surround the distal end of a probe unit, thereby covering an articulate mechanism 14 that is used for manipulating the head end of the probe. Inner boot 10 is totally surrounded by and encased within outer sleeve 12 to prevent any leakage of bodily fluids into the probe or any leakage of lubricating fluids from the internal parts of the probe into the body. The thicker, more resilient inner sleeve or boot 10 acts as a cushion that prevents relatively thin outer sleeve 12 from being pinched and torn or punctured by the elements of the articulate control mechanism 14 as the head of the probe is being manipulated. One or more transducers 16, or comparable devices, are affixed to the distal end of the probe unit. A bonding agent is used to secure outer boot 12 tightly around transducers 16 to prevent any interference with the ultrasound imaging. In addition, a third sleeve or boot 11 may be placed around transducers 16 to act as a shield against leakage of the glue or bonding agent. Electrical connections (not shown), typically comprising 64 coaxial cables for each transducer, connect transducers 16 to an external power supply and to appropriate monitoring equipment through a hollow tubular member 20. An epoxy seal 18 may be used to seal outer boot 12 to the distal end of member 20. The outer surface of sleeve 12 is preferably already very smooth and slippery or can be polished or specially treated to achieve a low-friction surface to facilitate insertion of the probe unit into a bodily cavity.

Articulate mechanism 14 for manipulating the head end of the probe is typically fashioned from interlocking stainless steel wires and rivets that define alternating open and closed sections of the mechanism as illustrated in FIG. 1. In manipulating this mechanism to orient the instrument head of the probe unit, one or more of the open sections of the articulate mechanism will partially or fully close, thereby creating the possibility of pinching or tearing outer sleeve 12 if outer sleeve 12 were not protected by the relatively thick, resilient inner boot 10. Articulate mechanism 14 can be controlled by thin control wires 22 connected to a rack and pinion system (FIG. 3), or equivalent control system, through member 20. By means of this control system, the head end of the probe can be bent or flexed 90 degrees or more as shown schematically in FIG. 2. As a result, transducers 16, or other medical instrument affixed to the end of the probe unit, can be manipulated within a small radius of curvature so as to scan over a range of plus or minus 90 degrees arc in one direction and plus 90 degrees to minus 110 degrees in the other direction. The problem with this system, as illustrated in FIG. 2, is that during bending, the outer elbow side of boot 10 experiences excessive stretching whereas the inner elbow side of boot 10 experiences a bunching (and therefore compression) of resilient material. In combination with the rigidity already inherent in the probe unit due to the articulate mechanism and coaxial cables, the stretching and bunching effects of the relatively thick inner boot 12 results in an excessive amount of force being required to overcome the rigidity which, in turn, puts unnecessary strain on thin control wires 22 thereby leading to fatigue and premature failure. The present invention overcomes this problem by reducing or eliminating the undesirable stretching and bunching effects of the inner boot 10.

FIGS. 3 and 4 schematically illustrate the operation of a conventional rack and pinion/wire control system for manipulation of the head end of a probe unit. Rack members 30 and 32 operate in reciprocating fashion as their respective teeth members engage the teeth members of pinion 34, thereby in turn operating wire members 22 connected to articulate mechanism 14. As illustrated in FIG. 4, by properly manipulating wire members 22, articulate mechanism 14 can be caused to bend a desired amount in a desired direction. The result is the ability to manipulate the head end of the probe unit, including a medical instrument affixed to the distal end of the probe, over a wide range of positions with a very small radius of curvature. Other conventional mechanisms for manipulating wire members 22 can be substituted for the rack and pinion system of FIG. 3 without departing from the scope of this invention.

FIG. 5 shows a schematic isometric view of a portion of the improved inner boot or sleeve 40 of the probe apparatus of this invention. Inner sleeve 40 takes the place of boot 10 in FIGS. 1 and 2. Sleeve 40 is relatively thick and relatively rigid compared with outer sleeve 12 which is thin, slippery, and readily flexible. The relative thickness and rigidity of sleeve 40 provides a high degree of structural support along the longitudinal axis of the probe unit, which facilitates insertion of the probe unit through the esophagus or other bodily canal without trauma to the body or damage to the probe unit. As discussed above with respect to boot 10, sleeve 40 also protects outer sleeve 12 from pinching by the elements of the articulate mechanism 14 as the head of the probe is manipulated. Such pinching of relatively thin sleeve 12 could result in a tear or puncture that would permit bodily fluid to leak into the interior of the probe or permit leakage of lubricating or other fluids from the interior part of the probe into the body. Sleeve 40 can be made from a wide variety of polymeric materials conventionally used for making catheters and the like, e.g. nylon, polyethylene, polyethylene terephthalate (PET), polyurethane, etc.

As shown in FIGS. 5 and 6, sleeve 40 includes a plurality of open, unfilled apertures 41, 42, 43, 44, 45, 46, 51, 52, 53, 54, 55 and 56 extending from the outer surface of sleeve 40 completely through to the hollow interior of sleeve 40. The apertures are located in varying positions around the circumference of sleeve 40. The apertures are also spaced apart laterally along the longitudinal axis 60 of sleeve 40. The function of the apertures appears to be that they dramatically reduce the force required to bend and manipulate the head portion of the probe unit by essentially eliminating the stretching and bunching effects described above in connection with FIG. 2. The use of such apertures in sleeve 40 has been found to dramatically and unexpectedly extend the life of the probe unit. Because the reduced life span of conventional transesophageal probes is believed to be due, in part, to a wide variety of factors, some of which—such as the total weight of the apparatus, the rigidity of the coaxial cables, and the reduced flexibility inherent in running 124 coaxial cables through a channel no larger than about 0.2 inches in diameter—are completely unrelated to the inner sleeve, the surprising effectiveness of an apertured inner boot in extending the life of the probe could not have been anticipated.

To a certain extent, these beneficial results can be realized with apertures of almost any size, shape and spacing provided there are enough of them and the apertures are large enough. These parameters can be established by routine experimentation. On the other hand, pinhole-sized apertures would provide essentially no reduction in the stretching and bunching effects described above and, therefore, would not work. Accordingly, the term "aperture" as used herein is meant to specifically exclude pinhole-sized apertures, such as those that might be used in a catheter, as discussed in connection with the prior art cited above, for purposes of providing fluid to or drainage of fluid from a bodily cavity. It has been found, however, that apertures having particular characteristics of size, shape and spacing produce unexpectedly improved results in minimizing the stress and strain on the wire control system of the probes of this invention. Thus, in a preferred embodiment of this invention, the apertures comprise wedge-shaped segments arranged in a particular configuration, all as described below.

For purposes of this application, the term "wedge-shaped segment" in reference to the apertures in inner sleeve 40 is meant to refer specifically and exclusively to an aperture having a lip-like shape generally as illustrated in FIGS. 5 and 6. Such a wedge-shaped segment is created by two planes intersecting a tubular surface and also intersecting each other so as to define a line of intersection which passes through two points on said tubular surface. The distance between the two points advantageously ranges from about 10-100%, preferably from about 50-100%, of the diameter of said tubular surface.

In another preferred embodiment of this invention, the tubular surface is a cylinder and the line of intersection intersects and is perpendicular to the center axis of the cylinder thereby creating what is referred to herein as a "normal wedge-shaped segment." It should be noted that a "normal wedge-shaped segment" as thus defined does not depend on the angle of the two intersecting planes vis-a-vis one another. In general, however, it is also preferred that the intersecting planes intersect at an acute angle so as to define an "acute wedge-shaped segment" wherein the sides of the wedge, as illustrated in FIG. 6, meet at an acute angle. The acute angle advantageously ranges from about 5-90 degrees, preferably from about 20-60 degrees. In accordance with the foregoing definitions, the apertures illustrated in FIG. 6 will be referred to as "acute, normal wedge-shaped segments" for purposes of this application.

For purposes of this application, the term "matched pair" in reference to the apertures in inner sleeve 40 is meant to refer specifically and exclusively to two apertures of substantially identical size and shape, positioned approximately 180 degrees apart around the circumference of the tubular surface of the inner sleeve, and also laterally spaced a distance from one another along the axis of the sleeve, generally as illustrated by matched pairs 41 and 42, 43 and 44, and 45 and 46 in FIG. 5, and matched pairs 51 and 52, 53 and 54, and 55 and 56 in FIG. 6. The two apertures comprising a matched pair, as defined above, are preferably laterally spaced as closely as possible without intersecting one another, the only limitation in this respect being that sufficient tubular material must be maintained between the apertures of a matched pair, as well as between adjacent matched pairs, to preserve the structural integrity of the inner sleeve during repeated bending operations. Such spacing can be determined for a given sleeve material and thickness by routine experimentation.

In general, adjacent matched pairs of apertures should be positioned at different locations around the circumference of the inner sleeve. This configuration helps to insure increased flexibility of the system in every direction—i.e., the head of the probe can be flexed over a maximum range with minimal stress and strain on the wire controls. In a preferred embodiment that minimizes production costs and facilitates closer lateral spacing of matched pairs of apertures, adjacent matched pairs of apertures, such as 41, 42 and 51, 52 or 45, 46 and 55, 56 (FIG. 6) are positioned approximately 90 degrees apart around the circumference of the inner sleeve.

FIG. 7 illustrates how the apertured inner sleeve 40 of FIGS. 5 and 6 facilitates bending the head end of the probe apparatus with minimal stretching and bunching effects. Thus, as shown in FIG. 7, apertures 41, 43 and 45 along the outer elbow portion of the bent sleeve 40 open to a greater or lesser extent than usual to accommodate the bend, while apertures 42, 44 and 46 along the inner elbow portion of sleeve 40 close up to a greater or lesser extent than usual. The lip-shaped openings of apertures 41, 43 and 45 reduce or eliminate the stretching of sleeve material along this outer elbow that would otherwise occur. Similarly, the closing of lip-shaped apertures 42, 44 and 46 reduces or eliminates the bunching of sleeve material along this inner elbow that otherwise would occur (see FIG. 2).

FIG. 8 shows how apertured sleeve 40, as described above, can be substituted for inner boot 10 of FIG. 1 for use in connection with a transesophageal probe or comparable apparatus. Similar to the apparatus shown in FIG. 1, in FIG. 8 a relatively thin and slippery outer sleeve 12 and apertured inner sleeve 40 in accordance with this invention surround the distal end of the probe unit, covering articulate mechanism 14 and transducers 16. Because the apertures in sleeve 40 minimize stretching and bunching, the head of the probe unit can be repeatedly manipulated over a wide scanning range using control wires 22 while putting minimal stress and strain on the control wires. As a result, apertured sleeve 40 extends the useful life of this flexible probe apparatus substantially beyond that of comparable conventional probes.

Since certain changes may be made in the above-described apparatus without departing from the scope of the invention herein involved, it is intended that all matter contained in the above description shall be interpreted in an illustrative and not in a limiting sense.

Having described the invention, what is claimed is:

1. A flexible, manipulatable probe apparatus comprising in combination: probe means comprising an instrument head portion; control means for controlling the orientation of the head portion of said probe means from a location remote from said head portion; first sleeve means radially spaced apart from and independent of said control means for at least partially surrounding said control means; and second sleeve means for at least partially surrounding said first sleeve means, wherein said first sleeve means is relatively thicker than said second sleeve means and comprises a plurality of open apertures in proximity to the head portion of said probe means.

2. The probe apparatus of claim 1 further wherein said first sleeve means comprises a tubular shape.

3. The probe apparatus of claim 2 further wherein said apertures comprise wedge-shaped segments.

4. The probe apparatus of claim 2 further wherein said apertures comprise normal wedge-shaped segments.

5. The probe apparatus of claim 2 further wherein said apertures comprise acute, normal wedge-shaped segments.

6. The probe apparatus of claim 3 further wherein said apertures comprise matched pairs.

7. The probe apparatus of claim 6 further wherein adjacent matched pairs are positioned at different locations around the circumference of said first sleeve means.

8. The probe apparatus of claim 6 further wherein adjacent matched pairs are positioned approximately 90 degrees apart around the circumference of said first sleeve means.

9. The probe apparatus of claim 2 further wherein said apertures comprise matched pairs of wedge-shaped segments.

10. The probe apparatus of claim 2 further wherein said apertures comprise matched pairs of normal wedge-shaped segments.

11. The probe apparatus of claim 2 further wherein said apertures comprise matched pairs of acute, normal wedge-shaped segments.

12. The probe apparatus of claim 11 further wherein adjacent matched pairs of wedge-shaped segments are positioned approximately 90 degrees apart around the circumference of said first sleeve means.

13. In a probe apparatus comprising instrument means and instrument control means for orienting the instrument means from a remote location, and a thin, slippery outer sleeve to cover said instrument means and instrument control means, the improvement comprising a relatively thicker, resilient inner sleeve positioned between said instrument control means and said outer sleeve, wherein said inner sleeve is radially spaced apart from and independent of said instrument control means and comprises a continuous tubular surface having a plurality of open apertures adjacent to said instrument means.

14. The probe apparatus of claim 13 further wherein said inner sleeve comprises a tubular member and said apertures comprise wedge-shape segments.

15. The probe apparatus of claim 14 further wherein said apertures comprise matched pairs of wedge-shaped segment.

16. The probe apparatus of claim 15 further wherein adjacent matched pairs of wedge-shaped segments are positioned approximately 90 degrees apart around the circumference of said outer sleeve.

17. A protective sleeve for a probe apparatus comprising a hollow, elongated, continuous tubular surface of uniform sidewall thickness having a circular cross section and a plurality of lip-shaped apertures in its side wall each aperture perimeter serving to define a wedge-shaped segment, said apertures having a particular size, shape and spacing in order to minimize resistance to bending of said sleeve.

18. The protective sleeve of claim 17 further wherein said apertures comprise normal wedge-shaped segments.

19. The protective sleeve of claim 17 further wherein said apertures comprise matched pairs of wedge-shaped segments.

20. The protective sleeve of claim 19 further wherein adjacent matched pairs of wedge-shaped segments are positioned approximately 90 degrees apart around the circumference of said tubular surface.

21. Transesophageal probe apparatus comprising in combination: an instrument head; articulation means connected at one end to said instrument head and at the other end to connection means for controlling said articulation means so as to orient said instrument head from a remote location; first sleeve means surrounding but radially spaced from and independent of said articulation means; and second sleeve means surrounding said first sleeve means, wherein said first sleeve means is relatively thicker than said second sleeve means and comprises a continuous tubular surface having a plurality of lip-shaped apertures in its side wall, said apparatus being radially sized so as to slide inside a human esophagous.

22. Apparatus according to claim 21 further wherein said first sleeve means has a uniform sidewall thickness and a circular cross section.

23. Apparatus according to claim 21 further wherein said first sleeve means is relatively resilient and cushion-like compared with said second sleeve means.

24. Apparatus according to claim 21 further wherein said apertures are positioned at different locations around the circumference of said first sleeve means.

25. Apparatus according to claim 21 further wherein said apertures comprise adjacent matched pairs positioned approximately 90 degrees apart around the circumference of said first sleeve means.

* * * * *

UNITED STATES PATENT AND TRADEMARK OFFICE
CERTIFICATE OF CORRECTION

PATENT NO. : 5,235,964

DATED : August 17, 1993

INVENTOR(S) : Daniel Abenaim

It is certified that error appears in the above-identified patent and that said Letters Patent is hereby corrected as shown below:

Claim 15, column 8, line 50, delete "segment" insert -- segments --.

Signed and Sealed this

Fifteenth Day of March, 1994

*Attest:*

BRUCE LEHMAN

*Attesting Officer*     *Commissioner of Patents and Trademarks*